United States Patent [19]
Singh et al.

[11] Patent Number: 6,017,932
[45] Date of Patent: Jan. 25, 2000

[54] PHARMACEUTICAL COMPOSITIONS CONTAINING AT LEAST ONE NSAID HAVING INCREASED BIOAVAILABILITY

[75] Inventors: Amarjit Singh; Rajesh Jain, both of New Delhi, India

[73] Assignee: Panacea Biotec Limited, New Delhi, India

[21] Appl. No.: 08/988,211

[22] Filed: Dec. 10, 1997

[30] Foreign Application Priority Data

Dec. 12, 1996 [IN] India ............................... 2780/DEL/96

[51] Int. Cl.$^7$ ...................... A61K 31/445; A61K 31/415; A61K 31/18
[52] U.S. Cl. ........................... 514/321; 514/327; 514/330; 514/406; 514/605; 514/682
[58] Field of Search ..................... 514/321, 327, 514/330, 605, 682, 406

[56] References Cited

U.S. PATENT DOCUMENTS

| 5,283,261 | 2/1994 | Drago ...................................... 514/605 |
| 5,439,891 | 8/1995 | Kapil et al. ................................ 514/31 |

FOREIGN PATENT DOCUMENTS

| 0 709 098 A1 | 5/1996 | European Pat. Off. . |
| 2 662 360 | 11/1991 | France . |
| WO 91/17774 | 11/1991 | WIPO . |
| WO 94/28031 | 12/1994 | WIPO . |
| WO 95/34533 | 12/1995 | WIPO . |

OTHER PUBLICATIONS

John L. Wallace et al, "The Development of Gastrointestinal–Sparing Nonsteroidal Anti–Inflammatory Drugs", Trend Pharmacol Sci., 1994, 15, 405–406.

Jaime L. Masferrer et al, "Selective Inhibition of Inducible Cyclooxygenase 2 In Vivo is Antiinflammatory and Nonulcerogenic", Proc. Natl. Acad. Sci. USA, vol. 91, pp. 3228–3232, Apr. 1994.

Paul A. Insel, "Analgesic–Antipyretic and Antiinflammatory Agents and Drugs Employed in the Treatment of Gout", Goodman and Gilman's The Pharmacological Basis of Therapeutics, Hardman JG, Limbird Le (Eds) McGraw–Hill, New York, pp. 617–657.

E. Magni, "Nimesulide an Overview", Drug Invest 1991, 3 Suppl. 2:1–3.

E. Magni, "The Effect of Nimesulide on Prostanoid Formation", Drugs 1993, 46 Suppl. 1:10–4.

Usha Zutshi et al, "The Impact of Ayurvedic Herbals on Drug Bioavailability", Indian Drugs, 19(12), 476–479, 1982.

Alan Ward et al, "Nimesulide, A Preliminary Review of Its Pharmacological Properties and Therapeutic Efficacy in Inflammation and Pain States", Drugs 36: 732–753, 1998.

C.K. Atal et al, "Scientific Evidence on the Role of Ayurvedic Herbals on Bioavailability of Drugs", Journal of Ethnopharmacology, 4 (1981) 229–232.

*Primary Examiner*—Phyllis G. Spivack
*Attorney, Agent, or Firm*—Oblon, Spivak, McClelland, Maier & Neustadt, P.C.

[57] ABSTRACT

A novel composition for increasing the bioavailability of Non-steroidal Anti-inflammatory Drugs (NSAIDs), particularly those belonging to the category which exhibits its activity by selectively inhibiting cyclooxygenases-II (COX-II) and/or lipooxygenases, is disclosed. The composition is characterized in having clinically significant increased bioavailability when compared to the known compositions of the drugs. The pharmaceutical compositions comprise NSAIDs and Piperine, as herein disclosed. Enhanced bioavailability of NSAIDs results in the reduction of both dosages and dose-related side effects.

11 Claims, No Drawings

PHARMACEUTICAL COMPOSITIONS CONTAINING AT LEAST ONE NSAID HAVING INCREASED BIOAVAILABILITY

BACKGROUND OF THE INVENTION

The present invention relates to a novel composition for increasing the bioavailability of Non-steroidal Anti-inflammatory Drugs (NSAIDs) or derivatives thereof particularly those belonging to the category which exhibits its activity by selectively inhibiting cyclooxygenases-II (COX-II) and/or lipooxygenases. More preferably invention related to the drugs like Nimesulide, Nabumetone, Tepoxalin and Flosulide and/or derivatives thereof. The novel composition is characterised in having clinically significant increased bio-availability when compared to the known compositions of the drugs. More particularly the invention relates to a pharmaceutical composition containing NSAIDs such as Nimesulide, Nabumetone, Tepoxalin and Flosulide and/or derivatives thereof and Piperine, its metabolites, structural analogues or isomers of Piperine. The invention also encompasses Kits that may be used in the method of this invention. The Kits would contain one or more doses of NSAIDs and one or more doses of Piperine, its metabolites, structural analogues or isomers of Piperine.

Enhanced bio-availability results in the reduction of the dose of NSAIDs or derivatives thereof and hence will reduce the cost of therapy in diseases like arthritis which require long term therapies which results from the high cost of the drugs. Also as the cost of therapy will decrease, NSAIDs such as Nimesulide can be put to much wider use in newer indications. Enhanced bio-availability of NSAIDs results in the reduction of dose-related side effects.

DESCRIPTION OF THE PRIOR ART

The anti-inflammatory mechanism of NSAIDs is due to reduction in prostaglandin synthesis by the direct inhibition of cyclo-oxygenase (COX). COX exists in two forms—COX-I and COX-II (Wallace J L, Cirino G. The development of gastrointestinal sparing NSAIDs. *Trend Pharmacol Sci.*, 1994, 15, 405–406.). COX-I is found in most tissues and is involved in the physiological production of prostaglandins (PGs) (Masferrer J L, Zweifel B S, Manning P T et.al. Selective inhibition of inducible COX-II in vivo is anti-inflammatory and non-ulcerogenic. *Proc Natl Acad Sci USA.*, 1994, 91, 3228–3232). Inhibition of beneficial PG's in organs such as stomach and kidney can result in gastric lesions, nephrotoxicity and internal bleeding. On the other hand COX-II is cytokine-inducible and is expressed only in inflammatory cells (Masferrer J L, Zweifel B S, Manning P T et.al. Selective inhibition of inducible COX-II in vivo is anti-inflammatory and nonulcerogenic. *Proc Natl Acad Sci USA.*, 1994, 91, 3228–3232). The identification and seperation of constitutive (COX-I) and inducible (COX-II) enzymes have led to development of newer NSAIDs which selectively inhibit the detrimental COX-II and not the beneficial COX-I enzyme. Examples of these newer NSAIDs are Nimesulide, Flosulide and Nabumetone (Insel Pa., Analgesic-Antipyretic and anti-inflammatory agents. In Goodman and Gilmans "The Pharmacological Basis of Therapeutics" Hardman J G, Limbird L E (eds) McGraw-Hill, New York., 617pp). These drugs are being developed as non-ulcerogenic, GIT-sparing, anti-inflammatory agents. Nimesulide is a NSAID that also has antipyretic and analgesic properties. The compound is weakly acidic (pKa=6.5) and differs from other NSAIDs in that its chemical structure contains a sulfonanilide moeity as the acidic group. (Magni E. Nimesulide an overview. Drug Invest 1991;3 Suppl. 2:1–3).

Chemically Nimesulide is N-(4-nitro, 2-phenoxyphenyl) methanesulfonamide, with the following chemical structure:

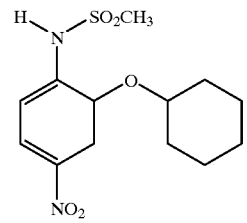

The therapeutic effects of NSAIDs are largely the result of their ability to inhibit prostaglandin synthesis via inhibition of cyclo-oxygenase. Unfortunately, this effect is also responsible for the inhibition of gastroprotective prostaglandins, which leads to gastrointestinal intolerance. In vitro, Nimesulide is a relatively weak inhibitor of prostaglandin synthesis and appears to exert its effects through a variety of mechanisms. (Magni E. The effect of nimesulide on prostanoid formation. Drugs 1993; 46 Suppl. 1:10–4) Indeed, the mechanism of action of this drug is more complex than previously thought and may involve interference with the production/action of mediators other than prostaglandins such as enzymes, toxic oxygen derivatives, cytokines, platelet-activating factor (PAF) and histamine.

Nimesulide is a novel non steroidal anti-inflammatory drug with better gastric tolerance than other commonly used NSAIDs. It acts mainly through selective COX II inhibition though additional mechanisms of action has been postulated. It has been found to be highly efficaceous in cancer pain etc and is comparable or superior to other NSAIDs like diclofenac or piroxicam in different pain models or models of inflammation.

Nimesulide has been given through oral and rectal route and its pharmacokinetic studies in case of these routes have been well documented. Our research group has demonstrated the use of Nimesulide through transdermal and Injectable formulation. (European patent application No. 96304460.7 and 96304461.5 and U.S. patent application Ser. No. 08/662,704 and 08/662,477 respectively).

The anti-inflammatory, analgesic and antipyretic activities of Nimesulide, a (NSAID) of the sulfonanilide class, have been demonstrated in a number of experimental models and in numerous clinical trials. Nimesulide has exhibited potency similar to or greater than that of indomethacin, diclofenac, piroxicam and ibuprofen in standard animal models of inflammation such as carrageenin-induced rat paw oedema and inflammation, ultraviolet light-induced erythema in guinea-pigs and adjuvant arthritis in rats.

The analgesic potency of Nimesulide was similar to that of ibuprofen and less than that of indomethacin in an acetic acid writhing tests in mice. Nimesulide has shown superior antipyretic potency to indomethacin, ibuprofen, aspirin and paracetamol (acetaminophen) in rats with yeast-induced fever.

Nimesulide is a relatively week inhibitor of prostaglandin synthesis in vitro and appears to exert its effects on histamine release, the neutrophil myeloperoxidase pathway, bradykinin activity, tumour necrosis factor-a release, cartilage degradation, metalloprotease synthesis, phosphodiesterase type IV inhibition, platelet aggregation and synthesis of platelet activating factor. Animal studies have suggested that nimesulide is less ulcerogenic than aspirin, indomethacin, naproxen, piroxicam and ibuprofen. Nimesulide appears to have little effect on renal prostaglandin synthesis in rats.

After oral administration of nimesulide 50 to 200 mg to healthy adult volunteers, peak serum concentrations of 1.98 to 9.85 mg/L are achieved within 1.22 to 3.17 hours. Compared with values obtained with oral drug administration, peak serum concentrations are slightly lower (2.14 to 2.32 mg/L) and are achieved more slowly (3 to 4.58 h) after rectal administration of nimesulide 100 and 200 mg. Oral drug absorption is nearly complete and concomitant administration of food may decrease the rate, but not the extent, of absorption of nimesulide. The drug is extensively bound (99%) to plasma proteins and has an estimated apparent volume of distribution of 0.19 to 0.35 L/Kg following oral administration.

Nimesulide is extensively metabolized (1 to 3% of dose is excreted unchanged in the urine) to several metabolites which are excreated mainly in the urine (~70%) or the feces (~20%). The drug is almost completely biotransformed into 4-hydroxy-nimesulide in both free and conjugated forms and this metabolite appears to contribute to the anti-inflammatory activity of the compound. Peak concentrations of 4-hydroxy-nimesulide ranged from 0.84 to 3.03 mg/L and were attained within 2.61 to 5.33 hours after oral administration of nimesulide 50 to 200 mg to healthy adult volunteers. The elimination half-life of 4-hydroxy-nimesulide ranges from 2.89 to 4.75 hours and is generally similar to or slightly higher than that of the parent compound (1.56 to 4.95 h).

The pharmacokinetic profile of nimesulide is not significantly altered in children, elderly volunteers and patients with moderately impaired renal function [creatinine clearance 1.8 to 4.8 L/h (30 to 80 ml/min]. Slight accumulation of 4-hydroxy-nimesulide was noted in patients with moderate renal impairment; however, the clinical significance of this finding is unknown.

Clinical studies have established the analgesic, anti-inflammatory and antipyretic effectiveness of orally (mostly 200 mg/day) or rectally (400 mg/day) administered nimesulide in the treatment of a variety of painful inflammatory conditions, including those associated with osteoarthritis, oncology, postoperative trauma, sports injuries, ear, nose and throat disorders, dental surgery, bursitis/tendinitis, thrombophlebitis, upper airways inflammation and gynecological disorders. In these indications, nimesulide is more effective than placebo and is at least as effective as therapeutic dosages of other NSAIDs, including piroxicam, ketoprofen, naproxen, etodolac, mefenamic acid, diclofenac, influmic acid, fentiazac, feprazone and flurbiprofen. Nimesulide therapy was characterised by a rapid onset of analgesia and symptomatic relief in studies where a significant difference in clinical efficacy between active treatments was observed.

Various attempts to improve the solubility and hence the bio-availability of Nimesulide have been reported. Pirotte Bernard et. al (WO 95/34533) have reported the formation of water soluble L-Lysine salt of Nimesulide. The salt was further complexed with Cyclodextrins. The more soluble form can be used to make dosage forms where solubilization is required. More soluble form is contempleted to have better bio-availability from solid dosage forms.

In U.S. Pat. No. 5,283,261 Filippo. Drago has reported the use of Dimethyl Sulphoxide to solubilize Nimesulide in treatment of Cataract. The approach is limited to used in topical or occular drug delivery.

Many workers have reported enhanced solubility and bio-availability of nimesulide by formation of inclusion compounds with various Cyclodextrins by Co-milling, Kneading or spray-drying techniques, e.g., Au Pat No. 7866591
FR Pat No. 2662360
Wo Pat No. 91/17774
Wo Pat No. 9428031

Chang, S F et. al. (Abstract No. 74 from proceedings of the Academy of Pharmaceutical Sciences. Atlanta Ga. 1975b) have reported a comparison between bio-availability of non-micronized and micronized tablets in dogs and human volunteers. Their findings showed significantly greater AUC values (approx 2 fold) and higher peak plasma concentrations with the micronized formulation.

The literature survey revealed that use of certain herbs, e.g., Piper longum and Piper nigrum as adjuncts in Indian System of medicine date back to 6th century Ad and 3rd century BC (Charaka, et al, Charak Samhita, 3rd edn, Nirnaya Sagar Press Bombay, 1991 (in Sanskrit), Kaviraj, K. B. Sushruta Samhita, 2nd ed., Chowk hamba Sanskrit Series, vol. 3, Varanasi, India 1953; Vagbmat, Ashtang Hridaya, Chowkhamba Sanskrit Series, Varanasi, India, 1962 (in Sanskrit).

Bose (Bose K. G. Pharmacopoeia Indica, Bose Laboratories, Calcutta, India 1928) makes a positive mention of the property of long pepper for increasing efficacy of Vasaka as antiasthmatic.

In an attempt to study scientific use of above herbs a research group (Usha Zutshi and J. L. Koul, Indian Drugs, 19 (12), 476479, 1982), observed the effect of Trikatu ( a composition comprising of Piper nigrum, Piper longum & Zingiber officinalis in equal proportion w/w) as a whole on vasicine resulting in enhanced bioavailability (and therefore the activity) of this drug to a great extent. Piper longum and Piper nigrum both are almost equally effective, whereas ginger (Zingiber officinalis) alone has no significant such enhancing effect.

In a recent art U.S. Pat. No. 5,439,891 the active constituent of Piper longum and Piper nigrum, Piperine, was shown to increase bio-availability of certain anti-tubercular and anti-leprosy drugs like Rifampicin, Isoniazid, Pyrazinamide, Ethambutol and Dapsone. The analysis of pharmacokinetic data shows that the mean increase in AUC for Rifampicin was 37.6%, Isoniazid was 131%, & Pyrazinamide was 36% when the formulations contained Piperine as a part of composition when compared with those which did not contain Piperine. The invention described in U.S. Pat. No. 5,439,891 is limited to demonstration of scope of use of Piperine as bio-availability enhancer in therapy of Rifampicin, Isoniazid, Pyrazinamide, Ethambutol and Dapsone only. It has been specifically referred to in this study that the synergistic activity of Piperine on drugs is not uniform and appears to be selective. This was based on the inventors finding that Piperine has no effect on enhancing the bio-availability of synthetic antidiabetic drugs such as tolbutamide.

U.S. Pat. No. 5,439,891 does indicate that Piperine may be useful as a bioavailability enhancer in drugs Rifampicin, Pyrazinamide, Isoniazid, Ethambutol and Dapsone. All these are low molecular weight drugs and none of these drugs have poor bioavailabilty like the one exhibited by NSAIDS particularly Nimesulide.

EPO application no. 94116731.4 and publication no. EP 0 709 098 A1 in the Patel, Modi et.al describes use of Piperine as bio-availability enhancer for several broad categories of drugs. There is also mention of Non-steroidal Anti-inflammatory drugs. However this EP application has not tested the utility of Piperine in the new classes of NSAIDs such as those disclosed in the present invention. Its is surprising that Patel, Modi et.al reported the human volunteer data in the European Application without any previous publication or reference of the animal data of such experiments. On critical examination of the specification the inventors also opine that the number of drugs for which increase in bio-availability has been reported appears to be unjustified in view of the human effort and time required for such experiments.

SUMMARY OF THE INVENTION

In accordance with present invention there is disclosed a composition of Piperine, its metabolites, structural analogues or isomers thereof along with atleast one NSAIDs which enhances the bio-availibilty of NSAIDs derivatives thereof.

DETAILED DESCRIPTION OF THE INVENTION

The incorporation of Piperine, its metabolites or structural analogues or isomers thereof with NSAIDs particularly Nimesulide or derivatives thereof results in a synergistic composition having unexpected increased bioavailability of NSAIDs particularly Nimesulide and derivatives thereof. Therefore the invention does not involve simple mixing of the components. It is also to be noted that Piperine or has no pharmacological properties but when mixed with NSAIDs particularly Nimesulide or derivatives thereof results in a synergistic effect on said NSIADs particularly Nimesulide causing enhanced activity and bio-availibilty thereof.

Piperine, (E, E) 1-[5-(1,3-benzodioxyl-5-yl)-1-oxo-2,4-pentadenyl] piperidine is the main constituent of many Piper species. It is mostly obtained from Piper longum (3–5%) or Piper nigrum (3–9%) which are cultivated commercially.

Piperine has the formula:

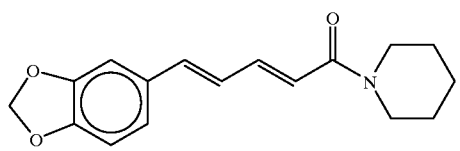
(1)

Examples of its metabolites are as follows:

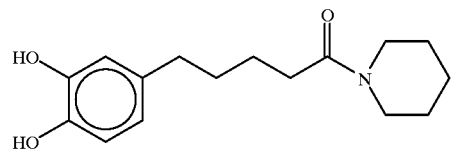
(2)

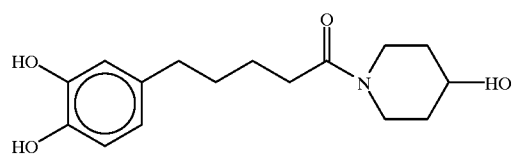
(3)

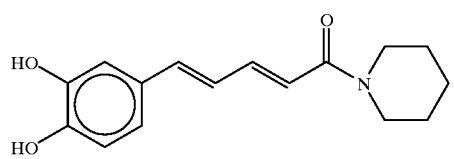
(4)

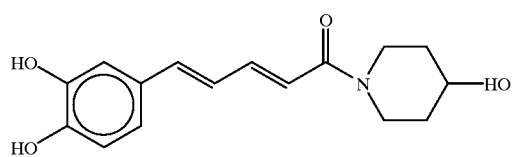
(5)

Piperine as a parent molecule and/or one or more of its metabolites and/or analogues thereof may have a role in enhancing bio-availability of drugs. Examples of Piperine analogues are derivatives in which the piperidine ring is substituted, e.g. by an amino group, or esters (e.g. $C_{1-6}$ alkyl esters) of metabolites containing an OH group.

Piperine forms monoclinic prisms from ethanol mp 130° C. It is tasteless at first but induces a burning sensation after a few seconds. It is neutral to litmus (pKa 12.22). It is soluble in benzene, chloroform, ether, ethyl acetate, dichloromethane, alcohol, acetic acid and insoluble in water, pet. ether.

On alkaline hydrolysis it furnishes a base piperidine and the acid viz. piperic acid, mp 216° C. It may be synthesized by condensing the two components under proper conditions.

It has the following spectral characteristics:
UV (methanol): max 340 mu (32,000).
IR(KBr): 1633, 1610, 1580, 1510, 1440, 1250, 1190, 1130, 1030, 995, 930, 842 $cm^{-1}$.

Piperine is commercially available. In addition, Piperine can be isolated from oleo-resin of Piper nigrum (Black pepper) or Piper longum (Long pepper). The powdered fruits of the plant (Piper nigrum) are extracted with dichloromethane at room temperature with stirring for 12 hours. The extract is filtered, concentrated in vacuum and the residue is subjected to purification on an alumina column. Pure Piperine can be obtained either from petroleum ether/ethyl acetate fractions or dichloromethane to give crude Piperine. Pure Piperine can be obtained by crystallization from ethanol. Piperine can also be obtained directly from the crude residue in lesser amounts by extraction in alcohol, filtration and successive crystallisation. Piperine metabolites, analogues and isomers can be prepared synthetically.

Preferably NSAIDs such as Nimesulide is present in the composition from 0.1 mg/kg body wt. to 6.0 mg/kg body Vt. and Piperine is 0.01 mg/kg body wt. to 10.0 mg/kg body wt.

Prefeably Nabumetone is present in the composition from 0.1 mg/kg body wt. to 50.0 mg/kg body wt. and Piperine is 0.01 mg/kg body wt. to 10.0 mg/kg body wt.

EXPERIMENT I

To demonstrate the effect of the novel composition, an experiment was conducted employing the composition containing Nimesulide with Piperine in a pre-determined dose on rats. The results of the experiment are illustrated in Table-1. It was found during administration of the composition of the invention on the experimental animals that increase in bio-availability will result in the reduction of dose and hence cost of therapy in long term diseases like arthritis. Also a reduction in dose related side-effects can be anticipated.

In order to prove the effect of Piperine on bio-availability of Nimesulide from its composition, albino rats of either sex of body weight 200 g±10 gms were taken. The rats were housed 5 per cage with food and water provided ad libidum.

On the day of experimentation the rats were randomised into ten batches of 5 rats each. Four groups were formed. Group I consisted of one batch of 5 rats, which was kept as control which received no drug treatment. Group II consisted of four batches of five rats each. This group was administered with Composition containing Nimesulide alone, at a dose level of 1.8 mg/Kg body wt, in the form of suspension of micronised drug in distilled water. Rats of batch I from Group II were sacrificed 60 minutes post treatment after Chloroform anaesthesia. Batch 2,3 and 4 were similarly sacrificed at 120 min., 240 min. and 360 min. post treatment respectively. Blood was collected from the rats from the ventricle into heparinised tubes.

Group III consisted of one batch of 5 rats, which received only Piperine at a dose level of 1.0 mg/kg body wt. The animals were sacrificed 160 minutes post treatment after Chloroform anaesthesia. Blood was collected from the rats from the ventricle into heparinised tubes.

Group IV consisted of 4 batches of 5 rats each. This group was administered with composition containing Nimesulide at a dose level 1.8 mg/kg body wt. and Piperine at a dose level 1.0 mg/kg body wt., in the form of suspension of micronised drugs in distilled water. Rats of batch 1 from Group IV were sacrificed 60 minutes post treatment after Chloroform anaesthesia. Batch 2, 3 and 4 were similarly sacrificed at 120 min., 240 min. and 360 min. post treatment respectively. Blood was collected from the rats from the ventricle into heparinised tubes.

The blood samples were centrifuged at 3700 rpm and the plasma separated. To 1 ml plasma 0.5 ml of HCl was added and then extracted with 2 ml of benzene. Extracted benzene was evaporated in a water bath at 95° C. and reconstituted with 100 µl of mobile phase and 10 µl was injected into the HPLC.

Waters HPLC fitted with $C_8$ µ Bondapack was used along with Waters UV-Vis detector (254 nm). Acetonitrile 50% with 50% Ammonium di-hydrogen Phosphate (0.01M) in double distilled, filtered (0.22 µ) water was used as the mobile phase.

The retention time for Nimesulide was 4.26 min. Unpaired student T test was applied on the data. Level of significance was fixed at p<0.05.

In the animals of Group I no peak corresponding to retention time of Nimesulide was seen. In the animals of Group II where composition containing Nimesulide alone was administered, the drug could be detected by 60 minutes of administration. The plasma levels reached at this point of time is 5.8±1.7 (S.D.) mg/ml of plasma. Statistically significant levels (P<0.05) were attained at 120 min. post treatment with drug concentration in plasma being 7.9±2.3 mg/ml. Concentration of the drug, at 240 min and 360 min. was 4.6±1.4 kg/ml and 2.2±1.1 mg/ml, respectively.

The present study demonstrates that significant amount of Nimesulide reaches the systemic circulation by 60 min. of administration of composition containing Nimesulide alone through the oral route and the drug levels can be seen till 360 min. post treatment. The study also demonstrates that when the composition containing Nimesulide alongwith Piperine is administered, the average plasma levels are 43% higher at 60 min, 95% higher at 120 min., 113% higher at 240 min. and 272% higher at 360 min. post treatment than the plasma levels obtained after administration of composition containing Nimesulide alone.

The data in provided herein above illustrates explicitly the inventors' findings that the addition of Piperine to Nimesulide enhances the bio-availability of Nimesulide significantly.

TABLE I

| | Plasma levels of Nimesulide (mg/ml) Post treatment time | | | |
|---|---|---|---|---|
| Group | 60 min. | 120 min. | 240 min. | 360 min. |
| Group I | — | — | — | — |
| Group II | 5.8 ± 1.7 | 7.9 ± 2.3 | 4.6 ± 1.4 | 2.2 ± 1.1 |
| Group III | — | Nil | — | — |
| Group IV | 8.3 ± 2.2 | 15.4 ± 3.3 | 9.8 ± 2.8 | 6.0 ± 1.9 |

EXPERIMENT II

In another set of experiments in mice, Nimesulide was administered alone and in combination with Piperine at sub-threshold dose level and compared with threshold level for the analgesic activity monitored be acetic acid induced writhing technique. Pharmacokinetic studies were also performed in rats. The aim of the experiments was to see whether Nimesulide when administered at low dosage level alongwith Piperine could produce significant pharmacological response or not.

The study design for acetic acid induced writhing in mice was as follows:

TABLE II

| GROUP No. | TREATMENT REGIME |
|---|---|
| I. | Vehicle treated (distilled water + gum acacia) - no drug |
| II. | Nimesulide (6.5 mg/kg) |
| III. | Nimesulide (10 mg/kg) |
| IV. | Nimesulide (10 mg/kg) + Piperine (1 mg/kg) |
| V. | Nimesulide (10 mg/kg) + Piperine (3 mg/kg) |
| VI. | Nimesulide (10 mg/kg) + Piperine (5 mg/kg) |
| VII. | Nimesulide (10 mg/kg) + Piperine (10 mg/kg) |
| VIII. | Nimesulide (6.5 mg/kg) + Piperine (10 mg/kg) |

The single test point pharmacokinetic studies were performed in two groups of rats. Group I received Nimesulide only at a dose of 10 mg/kg administered orally. Group II received Nimesulide (10 m/kg) with Piperine (10 mg/kg) administered orally. Rats were sacrificed at 90 minutes. post treatment and blood samples were analysed by HPLC.

The results of the acetic acid induced writhing produced very surprising results. Whereas Nimesulide above 6.5 mg/kg dose failed to show any analgesic activity; when administered alongwith Piperine produced significant analgesia.

The results of the experiment are given below

TABLE III

| PROTECTION AGAINST ACETIC ACID INDUCED WRITHING GROUPS (n = 8) | | |
|---|---|---|
| GROUP No. | TREATMENT REGIME | % PROTECTION |
| I. | Vehicle treated (distilled water + gum acacia) | 0% |
| II. | Nimesulide (6.5 mg/kg) | 17% |
| III. | Nimesulide (10 mg/kg) | 54% |

TABLE III-continued

PROTECTION AGAINST ACETIC ACID INDUCED WRITHING GROUPS (n = 8)

| GROUP No. | TREATMENT REGIME | % PROTECTION |
|---|---|---|
| IV. | Nimesulide (10 mg/kg) + Piperine (1 mg/kg) | 56% |
| V. | Nimesulide (10 mg/kg) + Piperine (3 mg/kg) | 72%** |
| VI. | Nimesulide (10 mg/kg) + Piperine (5 mg/kg) | 76%** |
| VII. | Nimesulide (10 mg/kg) + Piperine (10 mg/kg) | 87%*** |
| VIII. | Nimesulide (6.5 mg/kg) + Piperine (10 mg/kg) | 55%# |

*= $p < 0.001$, = $p < 0.01$; (#= $p < 0.01$ comparing Group VIII with Group II)

The results of pharmacokinetic studies corroborated the fact that Piperine causes increased bioavailability of Nimesulide. The Plasma concentrations of Nimesulide when administered with Piperine were higher than when Nimesulide was administered alone and this correlate well with the therapeutic analgesic action of the composition.

TABLE IV

Pharmacokinetic study in Rats

| | Groups | |
|---|---|---|
| | Nimesulide + Piperine | Nimesulide |
| Number of animals | 5 | 5 |
| Dosage | 10 mg/kg + 10 mg/kg | 10 mg/kg |
| Plasma concentration (90 min post treatment) | 11.485 mg/ml* | 8.818 mg/ml |

The invention will now be described with reference to the following examples.

Example - I
DIFFERENT COMPOSITIONS FOR TEPOXALIN AND PIPERINE CAPSULES

| Composition | 1 | 2 | 3 |
|---|---|---|---|
| Tepoxalin | 25 mg | 50 mg | 100 mg |
| Piperine | 2 mg | 5 mg | 10 mg |
| Lactose | 205 mg | 179 mg | 187 mg |
| Magnesium Stearate | 8 mg | 8 mg | 8 mg |
| Sodium Lauryl Sulphate | 2 mg | 3 mg | 5 mg |
| Total | 242 mg | 245 mg | 310 mg |

Example - II
DIFFERENT COMPOSITIONS FOR NABUMETONE TABLETS

| Composition | 1 | 2 | 3 |
|---|---|---|---|
| Nabumetone | 1000 mg | 50 mg | 1500 mg |
| Piperine | 100 mg | 5 mg | 150 mg |
| Starch | 97 mg | 150 mg | 110 mg |
| Microcyrstalline Cellulose | 100 mg | 114 mg | 115 mg |
| Polyvinyl Pyrrolidone | 18 mg | 5.0 mg | 30 mg |
| Magnesium Stearate | 15 mg | 3.0 mg | 20 mg |
| Purified Talc | 20 mg | 3.0 mg | 25.0 mg |
| Total | 1350 mg | 330 mg | 1950 mg |

Example III -
DIFFERENT COMPOSITIONS FOR KIT CONTAINING NIMESULIDE AND PIPERINE TABLETS.

Component 1

| | | |
|---|---|---|
| Nimesulide | — | 100 mg |
| Starch | — | 80 mg |
| Microcrystalline Cellulose | — | 120 mg |
| Polyvinyl Pyrrolidone | — | 4.0 mg |
| Magnesium Stearate | — | 3.0 mg |
| Purified Talc. | — | 3.0 mg |
| Colloidal Silicon Dioxide | — | 5.0 mg |
| Total | — | 315 mg |

Component 2

| | | |
|---|---|---|
| Piperine | — | 10 mg |
| Starch | — | 63 mg |
| Dicalcium Phosphate | — | 40 mg |
| Polyvinyl Pyrrolidone | — | 2.0 mg |

-continued

|  |  |  |
|---|---|---|
| Magnesium Stearate | — | 2.0 mg |
| Purified Talc. | — | 3.0 mg |
| Total | — | 120 mg |

Example - IV
DIFFERENT COMPOSITIONS FOR NIMESULIDE WITH PIPERINE TABLETS

| Composition | 1 | 2 | 3 | 4 | 5 | 6 | 7 | 8 |
|---|---|---|---|---|---|---|---|---|
| Nimesulide | 5 mg | 25 mg | 100 mg | 100 mg | 150 mg | 200 mg | 300 mg | 400 mg |
| Piperine | 1 mg | 5 mg | 100 mg | 1 mg | 50 mg | 50 mg | 100 mg | 25 mg |
| Starch | 160 mg | 135 mg | 35 mg | 100 mg | 35 mg | 85 mg | 65 mg | 41 mg |
| Microcrystalline cellulose | 80 mg | 80 mg | 40 mg | 74 mg | 35 mg | 35 mg | 100 mg | 100 mg |
| Dicalcium Phosphate | 64 mg | 65 mg | 43 mg | 43 mg | 36 mg | 36 mg | — | — |
| Purified Talc | 5.0 mg | 5.0 mg | 5.0 mg | 5.0 mg | 6.0 mg | 6.0 mg | 6.0 mg | 6.0 mg |
| Magnesium Stearate | 3.0 mg | 3.0 mg | 4.0 mg | 4.0 mg | 4.0 mg | 4.0 mg | 8.0 mg | 8.0 mg |
| Collidal Silicon Dioxide | 3.0 mg | 3.0 mg | 3.0 mg | 3.0 mg | 3.0 mg | 3.0 mg | 6.0 mg | 8.0 mg |
| Povidone | 4.0 mg | 4.0 mg | 5.0 mg | 5.0 mg | 6.0 mg | 6.0 mg | 15.0 mg | 12.0 mg |
| Total | 325 mg | 325 mg | 335 mg | 335 mg | 325 mg | 425 mg | 600 mg | 600 mg |

Example - V
DIFFERENT COMPOSITIONS FOR NIMESULIDE WITH PIPERINE CAPSULES

|  | 1 | 2 | 3 | 4 | 5 | 6 | 7 | 8 |
|---|---|---|---|---|---|---|---|---|
| Nimesulide | 100 mg | 50 mg | 150 mg | 200 mg | 250 mg | 300 mg | 300 mg | 400 mg |
| Piperine | 10 mg | 25 mg | 75 mg | 40 mg | 100 mg | 5 mg | 50 mg | 50 mg |
| Lactose | 140 mg | 160 mg | 57 mg | 54 mg | 150 mg | 140 mg | 125 mg | 100 mg |
| Collidal Silicon Dioxide | 5 mg | 5 mg | 8 mg | 8 mg | 8 mg | 10 mg | 5 mg | 5 mg |
| Purified Talc | 5 mg | 5 mg | 10 mg | 8 mg | 12 mg | 10 mg | 10 mg | 10 mg |
| Total | 260 mg | 245 mg | 300 mg | 310 mg | 520 mg | 465 mg | 490 mg | 565 mg |

Example - IV
DIFFERENT COMPOSITIONS FOR NIMESULIDE WITH PIPERINE TABLETS (COATED)

| Composition | 1 | 2 | 3 | 4 | 5 | 6 | 7 | 8 | 9 |
|---|---|---|---|---|---|---|---|---|---|
| Nimesulide | 100 mg | 100 mg | 150 mg | 50 mg | 25 mg | 200 mg | 300 mg | 400 mg | 25 mg |
| Piperine | 20 mg | 40 mg | 20 mg | 40 mg | 75 mg | 100 mg | 10 mg | 50 mg | 1 mg |
| Starch | 80 mg | 100 mg | 70 mg | 90 mg | 80 mg | 75 mg | 75 mg | 100 mg | 80 mg |
| Dicalcium Phosphate | 100 mg | 60 mg | 100 mg | 80 mg | 110 mg | 120 mg | 70 mg | 100 mg | 40 mg |
| Povidone | 6 mg | 8 mg | 10 mg | 6 mg | 8 mg | 10 mg | 10 mg | 10 mg | 12 mg |
| Magnesium Stearate | 10 mg | 10 mg | 10 mg | 8 mg | 10 mg | 8 mg | 10 mg | 10 mg | 12 mg |
| Purified Talc | 10 mg | 10 mg | 8 mg | 9 mg | 12 mg | 8 mg | 12 mg | 12 mg | 12 mg |
| Hydroxypropyl Methyl Cellulose | 15 mg | 20 mg | 15 mg | 25 mg | 30 mg | 25 mg | 50 mg | 40 mg | 60 mg |
| Polyethylene Glycol - 400 | 3 mg | 4 mg | 4.0 mg | 3.0 mg | 4.0 mg | 4 mg | 5 mg | 8 mg | 12 mg |
| *Isopropyl alcohol |  |  |  |  |  |  |  |  |  |
| *Methylene Chloride |  |  |  |  |  |  |  |  |  |
| Titanium Dioxide | 6 mg | 8 mg | 13 mg | 14 mg | 14 mg | 10 mg | 8 mg | 10 mg | 11 mg |
| Total | 350 mg | 380 mg | 400.0 mg | 325.0 mg | 325.0 mg | 560 mg | 550 mg | 740 mg | 255 mg |

* Lost during processing

Example - VII
DIFFERENT COMPOSITIONS OF NIMESULIDE WITH PIPERINE SUSPENSION

| Composition | 1 | 2 | 3 | 4 | 5 | 6 |
|---|---|---|---|---|---|---|
| Nimesulide | 1.0% w/v | 2.0% w/v | 0.5 | 3.0% w/v | 4.0% w/v | 4.0% w/v |
| Piperine | 0.1% w/v | 0.2% w/v | 0.02 | 0.5% w/v | 10% w/v | 0.2% w/v |
| Xanthan Gum | 0.3% w/v | 0.35% w/v | 0.3% | 0.3% w/v | 0.3% w/v | 0.25% w/v |
| Glycerol | 10.0% w/v | 15.0% w/v | 10.0% | 12.0% w/v | 15.0% w/v | 18.0% w/v |
| Cremophore RH-40 | 1.0% w/v | 1.0% w/v | 0.75% w/v | 10.25 | 1.25% w/v | 1.25% w/v |
| Sorbitol Solution | 30% w/v | 35% w/v | 30% w/v | 45% w/v | 50% w/v | 40% w/v |
| Colloidal silicon dioxide | 0.25% w/v | 0.25% w/v | 0.2% w/v | 0.25% w/v | 0.3% w/v | 0.35% w/v |
| Methyl Paraben Sodium | 0.18% w/v | 0.18% w/v | 0.15% w/v | 0.2% w/v | 0.2% w/v | 0.2% w/v |
| Propyl paraben sodium | 0.1% w/v | 0.1% w/v | 0.01% w/v | 0.1% w/v | 0.1% w/v | 0.09% w/v |
| Citric Acid | 3.0% w/v | 3.0% w/v | 3.0% w/v | 3.0% w/v | 3.0% w/v | 3.2% w/v |
| Flavour Mango | 0.15% w/v | 0.15% w/v | 0.1% w/v | 0.2% w/v | 0.2% w/v | 0.2% w/v |
| Colour Quinoline yellow | q.s | q.s | q.s | q.s | q.s | q.s |
| Purified Water | q.s to 100% | q.s. to 100% | q.s to 100% | q.s to 100% | q.s to 100% | q.s to 100% |

The examples of formulation given above should not be construed to limit the scope of the invention. In fact following these examples, any suitable or desired Pharmaceutical formulation containing a NSAID particularly Nimesulide can be prepared.

The composition of the invention can be in any form commonly employed for administration i.e. drink solution, a concentrated drink solution to be diluted before use, solution encapsulated in soft gelatin capsules, solution adsorbed on suitable adsorbents leading to formulations such as tablets, capsules and granules, the solution freeze dried for oral, topical solution or Injectable dosage forms and the like.

The composition according to this invention can be formulated to be administered topically, orally, rectally, vaginally, parenterally, by inhalation or by any other conventional method of administration. Also any other pharmaceutical form(s) known to the persons qualified in the art e.g. effervescent tablets, fast dissolving products, sustained release/controlled release/zero-order release products and alike can be construed. Another embodiment of this invention is a kit which comprises one or more pharmaceutically acceptable doses of NSAIDs or derivatives thereof or a mixture thereof and one or more pharmaceutical doses of Piperine, its metabolites, structural analogues, isomers thereof or a mixture thereof.

We claim:

1. A pharmaceutical composition having increased therapeutic efficacy comprising at least one NSAID selected from the group consisting of Nimesulide. Nabumetone, Tepoxalin, and Flosulide as active ingredient and a piperine selected from the group consisting of compounds of the following formulas:

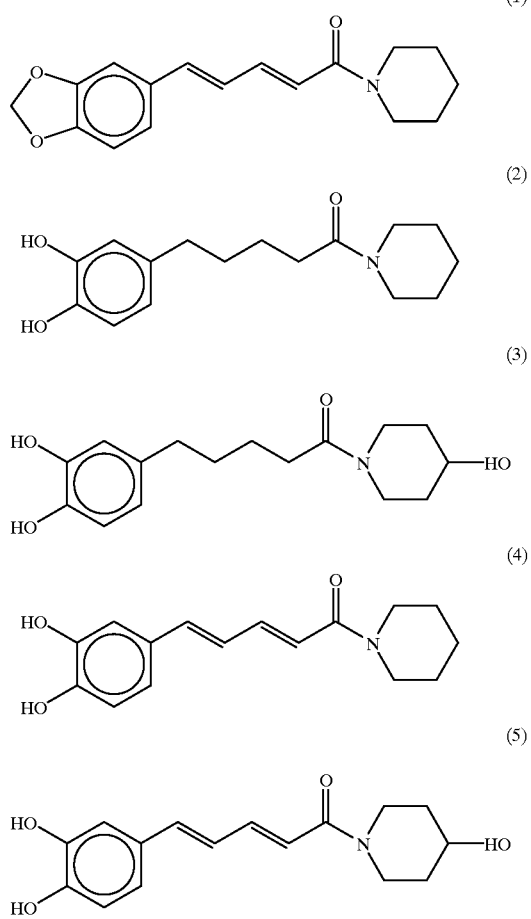

and derivatives thereof where the piperidine ring is amino-substituted; and derivatives thereof where the OH groups are replaced by $C_{1-6}$ alkyl esters.

2. A composition as claimed in claim 1 comprising an NSAID and piperine having the formula

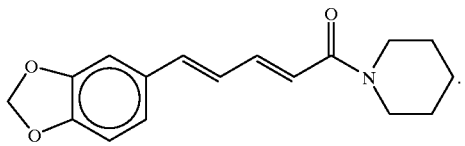

3. A composition according to claim 1, wherein the NSAID comprises Nimesulide.

4. A pharmaceutical composition as claimed in claim 1 in the form of a liquid preparation, tablet, capsule or granule.

5. A pharmaceutical composition as claimed in claim 1 in the form of a suspension of the active ingredients.

6. A pharmaceutical composition as claimed in claim 1 wherein the NSAID is present in an amount ranging from 0.1–50 mg/Kg body weight and the piperine is present in an amount ranging from 0.01–10 mg/Kg body weight.

7. A kit comprising one or more pharmaceutically acceptable doses of an NSAID selected from the group consisting of Nimesulide, Nabumetone. Tepoxalin and Flosulide and one or more pharmaceutically acceptable doses of a piperine selected from the group consisting of compounds of the following formulas:

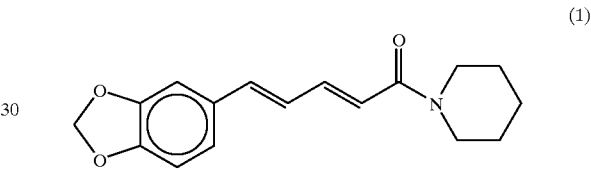

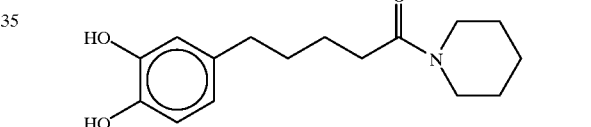

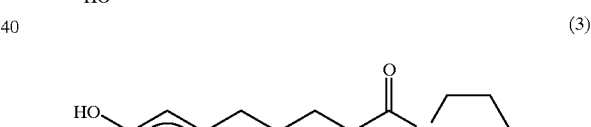

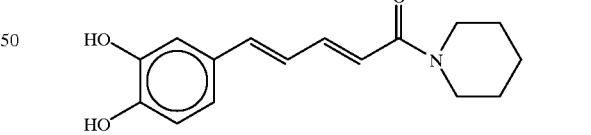

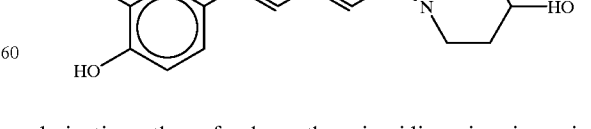

derivatives thereof where the piperidine ring is amino-substituted; and derivatives thereof where the OH groups are replaced by $C_{1-6}$ alkyl esters.

8. A kit according to claim 7, wherein the NSAID comprises Nimesulide.

9. A kit as in claim 7 wherein the pharmaceutically acceptable doses are in the form of a liquid preparation, tablet, capsule or granule.

10. A kit as claimed in claim 7 wherein the pharmaceutically acceptable doses are in the form of a suspension of the active ingredients.

11. A kit as claimed in claim 7 wherein the NSAID is present in an amount ranging from 0.1–50 mg/Kg body weight and the piperine is present in an amount ranging from 0.01–10 mg/Kg body weight.

* * * * *